United States Patent [19]

Horan et al.

[11] Patent Number: 4,783,401
[45] Date of Patent: Nov. 8, 1988

[54] VIABLE CELL LABELLING

[75] Inventors: Paul K. Horan, West Chester; Bruce D. Jensen, King of Prussia; Sue E. Slezak, Downingtown, all of Pa.

[73] Assignee: SmithKline Beckman Corporation, Philadelphia, Pa.

[21] Appl. No.: 925,192

[22] Filed: Oct. 31, 1986

[51] Int. Cl.$^4$ .................. C12Q 1/04; C12Q 1/16
[52] U.S. Cl. .................. 435/34; 424/3; 424/7.1; 424/1.1; 424/51; 424/9; 424/52; 435/35; 514/5; 514/735; 430/578; 544/253
[58] Field of Search .................. 424/3, 7.1, 1.1, 51, 424/9, 52; 435/34, 35; 514/5, 735; 430/578; 544/253

[56] References Cited

U.S. PATENT DOCUMENTS 4,343,782  8/1982  Shapiro .................. 424/3
4,424,201  1/1984  Valinsky et al. .................. 424/3

OTHER PUBLICATIONS

Fox, I. J., et al., *Proc. Mayo Clinic* 32:478–484 (1957).
Schad, H., et al., *Pfluegers Arch. Eur. J. Physiol.* 370(2):139–144 (1977).
Wanda, P. E. and Smith, J. D., *J. Histochem. Cytochem.* 30:1297–1300 (1982).
Axelrod, D., *Biophysical J.*, 26:557–574 (1979).
Honig, M. G. and Hume, R. I., *J. Cell Biology*, 103:171–187 (1986).
Johansson, L. B. A., et al., *J. Chem. Soc.*, Faraday Trans. 1:81(6):1389–1400 (1985).
Sims, P. J., Waggoner, A. S., Wang, C-H, and Hoffman, J. F.: Studies on the Mechanism by which Cyanine Dyes Measure Membrane Potential in Red Blood Cells and Phosphadidyl Doline Vesicle. Biochemistry, vol. 13(16) 3315–3330 (1974).
Jakoby, W. B. & Pastan, I. H.: Cell Culture (Methods in Enzymology) Academic Press (N.Y., San Francisco, London) 1979, pp. 52, 73, 136–137.
Stedman's Medical Dictionary, Williams & Willcins, 1980 p. 732.

*Primary Examiner*—Frederick E. Waddell
*Attorney, Agent, or Firm*—Stuart R. Suter; Alan D. Lourie; Janice E. Williams

[57] ABSTRACT

Methods for reproducibly labelling viable cells with cyanine dyes that do not significantly affect cell viability. Applications for labelled cells include using labelled red blood cells to distinguish post-transfusional bleeding from immunologic reaction and using dilution to measure growth rate of cultured cells.

26 Claims, No Drawings

VIABLE CELL LABELLING

BACKGROUND OF THE INVENTION

1. Field of the Invention

This invention relates to novel procedures that provide for labelling viable cells without adversely affecting cell morphology or function.

BACKGROUND INFORMATION

Fluorescence detection methods are used throughout Immunology and Cell Biology as analytical tools to measure specific properties of many cells. The advantage of fluorescence measurements is that a single dye molecule can be excited and return to the ground state thousands of times per second emitting as many photons of light. Thus, if a single antibody molecule is labelled with two or three dye molecules, several thousand photons of light can be obtained from a single antigen-antibody binding site. This is an enormous signal enhancement technique.

Dioxacarbocyanine dyes have been used to permit determinations of white blood cell differentials. Gunter Valet, Max Planck Ges Wsssensch; Patent Accession Number 84-102307/17, *Simultaneous Quantitative Determination of Blood Cells by Selective Staining and Measuring Volume and Fluorescence.* The dyes utilized in these studies, e dyes (less than 10) however, are short chain carbocyanine (less than 10) and respond to changes in membrane potentials. Furthermore, the short chain carbocyanine dyes enter cell mitochondria, are cytotoxic, and when the cells are washed the dyes easily leak out of the cell whether or not the membrane potential of the cell is changed. The long chain dyes of this invention are confined to the cell membranes and are only very minimally affected by membrane potential. They do not leak out of cells.

Other types of dyes used to achieve a white blood cell differential are not of the cyanine type and do not partition into lipids. The pyrilius or thiapyrilius compounds have been used to differentiate classes of white blood cells (David S. Frank, R. T. Belly, Patent Accession Number 84-166275/27, *Distinguishing Cells in Biological Samples by Staining With Pyrylium or Thiapyrylium Compounds.* These stains, however, bind to cytoplasmic and nuclear elements of the cell; they do not bind specifically to cell membranes. Other cationic dyes (L. Kass, Patent Accession Number 81-78187/43, *Determination of Different Leucocyte Categories by Staining with Meta:-Chromatic Cationic Dyes,* L. Kass, U.S. Pat. No. 4,400,370, August 23, 1983, *Metachromatic Dye Sorption Means for Differential Determination of Leukocytes,* L. Kass, Patent Accession Number 83-771982/39, *Analysis of Human Blood Cells By Staining Unfixed Cells With Specified Basic Dyes*) have been used to perform white blood cell differentials, however, these dyes do not partition significantly into membrane lipids but stain various organelles within the cell. Another metachromatic dye used to perform white blood cell differentials is acridine orange (P. J. Natale, U.S. Pat. No. 4,336,029, June 2, 1982, *Method and Reagents For Quantitative Determination of Reticulocytes and Platelets in Whole Blood,* R. J. Gershman, U.S. Pat. No. 4,325,706, Apr. 20, 1982, *Automated Detection of Platelets and Reticulocytes in Whole Blood*). Acridine orange stains the RNA and DNA of a cell and does not partition significantly into membrane lipids.

Another application makes use of merocyanine 540 to distinguish normal cells from malignant cells. This dye has a hydrophilic group at the end of the hydrocarbon tail and is cytotoxic when the cell is exposed to light. Valinsky, J. E., Reich. E. and Easton, T. G., U.S. Pat. No. 4,424,201, Jan. 3, 1984, *Employment of a Merocyanine Dye for the Detection of Malignant Leukocytic Cells.* Merocyanine is differentially incorporated into the membranes of normal and malignant cells.

Cyanine dyes of the short aliphatic chain length are used in a number of biological assays. These short aliphatic chain molecules, however, respond to membrane potentials and cross the cell membrane, penetrating into the mitochondria of the cell. H. M. Shapiro, U.S. Pat. No. 4,343,782, Aug. 10, 1982. The short chain cyanine dyes also are toxic to the cells and can not be used to track cells in vivo since they rapidly leak out of cells.

Tricarbocyanine dyes (Fox, I. J., et al., *Proc. Mayo Clinic* 32:478-484, 1957) and Evans-blue dye (Schad, H., et al, *Pfluegers Arch Eur J. Physiol* 370(2):139-144, 1977) have been used in vivo to estimate cardiac output by a dilution method. Dow (Dow, P., *Physiol. Rev.* 36: 77-102, 1956) describes the method as an injection of a known amount of some intravascular indicator on the venous side of the lungs, and measurement of the time course of arterial concentration of the indicator to determine the volume between the points of injection and sampling. These dyes are not used to stain cells.

Long chain aliphatic derivatives of fluorescein and Rhodamine have been used to monitor cell fusion (Wanda, P. E. and Smith, J. D., *J. Histochem. Cytochem* 30: 1297-1300, 1982). These dyes, however, contained only one aliphatic carbon chain and are not stable in the membrane for long periods of time. Furthermore, the method of detection of heterkaryon formation was resonance energy transfer between the two dye molecules. In addition, the staining was carried out in saline and no understanding of the solubility was revealed.

Biophysicists have used the major application of dialiphatic cyanine dyes of the long chain type to study the cell membrane fluidity (D. Axelrod, *Biophysical J.,* 26 557-574, 1979). In these types of studies the dye is applied to cells in short term culture from an ethanol stock. It was reported by several investigators that the variability in staining was very large. For biophysical measurements, however, it is necessary to look at only a few cells where each cell studied was measured several times. Also, long chain carbocyanine dyes that become incorporated into plasma membranes have been used to determine the original identity of neurons in culture. Honig, M. G. and Hume, R. I., *J. Cell Biology* 103:171-187 (1986). Absent from the above references is a uniform method of staining viable cells without adversely affecting cell morphology or function.

SUMMARY OF THE INVENTION

Presently invented are novel procedures that make possible consistent and reproducible labelling of viable cells without significantly altering cellular morphology or function. According to the present invention, cells are labelled with a cyanine dye having sufficient lipid solubility and a sufficiently high cell membrane partition coefficient to minimize or prevent dye molecule migration from cell membranes. Consistent and reproducible labelling is achieved by adding dye to cells suspended in medium containing an osmolarity regulating agent that does not significantly affect cell viability and in which the dye is soluble. Such osmolarity regulating agents include sugars, sugar-alcohols, amino acids, and certain hydrogen ion buffers ("Good's Buffers").

DETAILED DESCRIPTION

In the presently invented procedure for labelling various cells without adversely affecting cellular morphology or function, cyanine dyes are used. Compounds having the following structure are referred to herein as cyanine dyes:

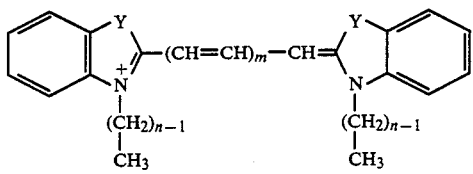

in which:
Y is oxygen, sulfur, methylene or alkylsubsubstituted methylene;
m is 0–3; and
n is 12–22.

As used herein, alkyl-substituted methylene refers to mono- or di- substituted methylene having any combination of methyl, ethyl, or propyl substituents.

Compounds of the above structure are referred to by the following generally understood shorthand formula:

$DiYC_n(2m+1)$

Sims, P. J., et al.; Biochem, 13:3315 (1974). Thus, for example, the compound wherein Y is sulfur and having three carbons bridging the rings and two fourteen carbon aliphatic chains is referred to as $DiSC_{14}(3)$. Similarly, $DiIC_{14}(5)$ indicates the compound wherein Y is isopropyl, and having five carbons bridging the rings and two fourgteen carbon aliphatic chains.

Included within compounds referred to herein as cyanine dyes are compounds of the above structure having one or more substitutions provided such substituted compounds are soluble in cell labelling media for at least as long as needed for labelling and have a sufficiently high cell membrane partition coefficient to remain associated with labelled cell membranes. Such compounds also must not significantly affect cell viability in the concentrations required for labelling. Solubility in cell labelling media is determined as shown below by dispursing a cyanine dye in the labelling media and, by standard sectrofluorometric techniques, measuring cellular fluorescence intensity over time. Decreasing fluorescence intensity indicates dye precipitation and adherence to vessel walls. Whether the dyes remain associated with cell membranes is determined, for example, using known flow cytometric procedures to monitor fluorescence intensity of red blood cells reinjected into the donor animal after labelling. Essentially constant fluorescence intensity of the labelled cells after reinjection establishes stability of the dye in cell membranes.

Also included within compounds referred to herein as cyanine dyes are compounds of the above structure that incorporate an atom which can be detected by nuclear magnetic reasonance imaging. Such compounds are prepared, for example, by incorporating a fluorine atom into one of the methyl groups of the aliphatic chains. Compounds of the above structure tagged with a gamma emitter such as $125_I$ also are referred to herein as cyanine dyes.

Cyanine dyes used in the present invention can be purchased from various sources such as Molecular Probes, Inc., Eugene, Oreg., and can be prepared from available starting materials using known synthetic methods. Hamer, F. M., The Cyanine Dyes and Related Compounds, Interscience Publishers (1964).

Using the invented procedures any viable cell can be labelled with cyanine dyes. As used herein, the term cell includes procaryotic cells such as bacteria, nucleated eukaryotic cells such as white blood cells, various tumor cells, and mammalian cells in culture, for example, chinese hamster ovary cells, yeast, and non-nucleated cells such as red blood cells and platelets. A nucleated cell is viable if it is able to grow or function essentially as expected for cells of its type; a non-nucleated cell is viable if it is able to perform its expected functions, for example a viable red cell is able to transport oxygen and carbon dioxide; and viable platelets perform essentially as expected in, for example, aggregation and release assays.

Cell labelling is performed in a medium that is non-lethal to cells and that provides for reproducible cell labelling. To give the medium the necessary characteristics, osmolarity regulating agents in which cyanine dyes form stable solutions for at least as long as required for labelling are used. Acceptable osmolarity regulating agents include agents or combination of agents such as sugars, for example monosaccharides such as glucose, fructose, sorbose, xylose, ribose, and disaccharides such as sucrose, sugar-alcohols, such as mannitol, glycerol, inositol, xylitol, and adonitol, amino acids such as glycine and arginine and certain Good's buffers such as N-tris(hydroxymethyl)-methyl-3-aminopropanesulfonic acid and those listed in Table II, below. Good, N. E., et al., Biochem. 15, 467–477 (1966), Good, N. E. and S. Izawa, Methods Enzymol., 24, Part B, 53 (1968), Feguson, W. J., et al., Anal. Biochem. 104:301–310 (1980). Some cell lines, however, may be sensitive to one or more of the osmolarity regulating agents, especially sugar-alcohols. Thus, prior to labelling, standard tests are conducted to make certain that the cells are viable in the intended osmolarity regulating agent. Additionally, small amounts of buffering agents may be added to the labelling medium to regulate hydrogen ion concentration.

The effect on cell viability of exposure to a variety of osmolarity regulating agents was determined by measuring the doubling time of Yac cells after the cells were exposed for thirty minutes to a variety of osmolarity regulating agents. Yac cells are a mouse lymphoma tissue culture cell line publically available from the American Type Culture Collection and is described by Kiessling, R., European J. Immunology 5:112–117 (1975). As the data shown in Table 1 demonstrate, when compared to phosphate buffered saline, exposure to sucrose, glucose, and the Good's buffers: TAPS, CAPS, EPPS, HEPPSO, and DIPSO resulted in negligable effects on cell doubling time which indicates the absence of exposure-related cellular toxicity.

TABLE 1

| Osmolarity Regulating Agent | Doubling Time (Hours) |
|---|---|
| Phosphate Buffered Saline | 31.0 |

TABLE 1-continued

| Osmolarity Regulating Agent | Doubling Time (Hours) |
|---|---|
| Sucrose | 41.0 |
| Glucose | 34.5 |
| TAPS | 32.7 |
| CAPS | 45.8 |
| EPPS | 32.2 |
| HEPPSO | 23.4 |
| DIPSO | 36.7 |
| 3-Amino-1-propanesulfonic acid | 99.6 |
| Sodium 3-(N—morpholino)propanesulfonic acid (MOPS) | A |
| 2-Amino-2-methyl-1,3-propanediol | B |
| 2-Amino-2-methyl-1-propanol | B |
| N—tris(hydroxymethyl)methylaminoethane-sulfonic acid (TES) | B |
| N,N—bis(2-hydroxyethyl)-2-aminoethane-sulfonic acid (BES) | A |
| 3-(Cyclohexylamino)-2-hydroxy-1-propane-sulfonic acid (CAPSO) | A |
| Triethanolamine | B |
| Tris(hydroxymethyl)aminomethane (TRIZMA) | B |
| Bis-tris propane | B |
| 2-(N—morpholino)ethanesulfonic acid (MES) | B |
| 3-[Dimethyl(hydroxymethyl)methylamino]-2-hydroxypropanesulfonic acid (AMPSO) | A |
| N,N—bis(2-hydroxyethyl)glycine (BICINE) | 57.7 |
| 3-[(-3-Cholamidopropyl)dimethylammonio]-1-propanesulfonate (CHAPS) | B |
| 3-[N—tris(hydroxymethyl)methylamino]-2-hydroxypropanesulfonic acid (TAPSO) | 63.6 |
| 3-(N—morpholino)-2-hydroxypropane-sulfonic acid (MOPSO) | 178.4 |
| 2-[(2-Amino-2-oxoethyl)amino]ethane sulfonic acid (ACES) | 1038.4 |
| Bis(2-hydroxyethyl)imino-tris-(hydroxymethyl)methane (BIS-TRIS) | A |
| 2-(N—cyclohexylamino)ethane sulfonic acid (CHES) | 51.5 |
| N—tris-(hydroxymethyl)methylglycine (TRICINE) | A |
| Glucosamine | 288.4 |
| Imidazole | B |
| Glycylglycine | 66.9 |

A—No growth or partially cytotoxic
B—Acutely cytotoxic

Table II shows various osmolarity regulating agents that were examined for cyanine dye solubility. All measurements of concentration were made after removal of precipitates by centrifugation and dissolving small aliquots of osmolarity regulating agents containing cyanine dyes into ethanol for spectrofluorometric analysis. The dyes used were $DiSC_{14}(5)$ and $DiOC_{14}(3)$, and the osmolarity regulating agents were at iso-osmotic concentrations. Reductions in fluorescence intensity from the ethanol solution standard directly correlate with reductions in cyanine dye solubility.

TABLE II

| Osmolarity Regulating Agent | Relative Fluorescence Intensity (CONC) | |
|---|---|---|
| | $DiSC_{14}(5)$ | $DiOC_{14}(3)$ |
| Ethanol | 100 | 100 |
| Glucose | 31 | 100 |
| Fructose | 35 | 100 |
| Sorbose | 40 | 100 |
| Sucrose | 41 | 100 |
| Xylose | 36 | 19–52 |
| Ribose | 24 | 100 |
| Lyxose | 0.12 | 1.8 |
| Glycine | 31 | 93 |
| Arginine | 17 | 17.2 |
| Glycerol | 39 | 99.5 |
| Inositol | 42 | 92 |
| Xylitol | 34 | 76.4 |
| Mannitol | 29 | * |
| Adonitol | 34 | ND |
| Tris(hydroxymethyl)-methylaminopropane sulfonic acid (TAPS) | 18 | ND |
| 3-(Cyclohexylamino)-1-propanesulfonic acid (CAPS) | 40 | ND |
| N—(2-Hydroxyethyl)piperazine-N'—3-propanesulfonic acid (EPPS) | 18 | ND |
| N—2-hydroxyethylpiperazine-N'—2-hydroxypropane-sulfonic acid (HEPPSO) | 20 | ND |
| 3-[N—N—bis(2-hydroxyethyl) amino]-2-hydroxypropane-sulfonic acid (DIPSO) | 43*** | ND |
| NaCl | 6 | 1.7 |
| Phosphate Buffered Saline | 2.1 | 6.5 |
| $Na_2SO_4$ | 7.4 | 1.6 |
| NaI | 1.1 | 0.14 |
| Choline Chloride | 11** | 6.3 |
| Choline Iodide | 0.16 | 2.3 |

*Precipitate in ethanol, no data obtainable.
**Artifact due to large crystals that did not pellet.
***Precipitate in ethanol (data questionable).
ND Not Determined As can be seen from Table II, cyanine dyes are much less soluble in the presence of classical salts than in the presence of sugars, except lyxose, sugar-alcohols, amino acids, and the Good's buffers, TAPS, HEPPSO, DIPSO, CAPS, and EPPS. Additionally, stability of $DiSC_{14}(5)$ solutions in sugars such as glucose, fructose, ribose, sorbose, sucrose, and xylose, sugar-alcohols such as glycerol, inositol, xylitol, and adonitol, and amino acids such as glycine and arginine was determined. The cyanine dye was stable in the tested solutions for at least twenty minutes, which is sufficient time for reproducible labelling, and in many of the agents the amount of cyanine dye in solution had not significantly decreased at sixty minutes.

Further, the solubility of cyanine dyes in a medium containing classical salts and osmolarity regulators in which the dyes are soluble was evaluated. The solubility of $DiSC_{14}(5)$ in iso-osmotic glucose solution was not significantly affected by dilution with distilled water. $DiSC_{14}(5)$ solubility in iso-osmotic glucose solution, however, was reduced significantly by dilution with only approximately 20% iso-osmotic sodium chloride solution. Thus, reproducible cell labelling with cyanine dyes can be performed in media containing no more than small amounts of classical salts, such as sodium chloride, potassium chloride, calcium chloride, sodium acetate, potassium acetate, sodium sulfate, sodium iodide, choline chloride, or choline iodide, and preferably is performed in a medium in which no classical salts are used to regulate osmolarity.

Cells cyanine dye labelled using the presently invented procedure were analyzed to determine the effect of labelling on cell viability. V79 cells which are available from the American Type Culture Collection, Rockville, Md., and are described in Prescott, D. M., Ann. New York Acad. Sci., 397:101–109 (1982), were labelled with a solution containing $DiOC_{14}(3)$ at a concentration of $10^{-5}$ or $4 \times 10^{-5}$M and the growth kinetics of the stained cells were compared to unstained cells and an equal mixture of stained and unstained cells. Cell doubling time was unaffected by cyanine dye labelling. Thus, labelling had no effect on cell growth. Also, several other standard tests of cell viability such as Trypan Blue Exclusion and Propidium Iodide exclusion confirmed an absence of effect on cell viability of cyanine dye labelling according to the described procedures.

The effect of cyanine dye labelling on cell viability also was determined by measuring red cell fragility. Labelled and unlabelled red blood cells were suspended in a sodium chloride medium of varying osmotic strengths by varying the salt concentration. Volume distributions of the cells were measured using a Coulter Counter ® with a channelizer attachment. Mean volumes were determined and plotted for each salt concentration, and volumes were increased as the sodium chloride concentration decreased until approximately 0.5 grams/100 ml where the volume displays a precipitous drop. At this point, the red cells lyse. Furthermore, the volume changes were the same whether or not the cells were labelled with a cyanine dye.

Similarly, in parallel samples, hemolysis was monitored as a function of sodium chloride concentration. After the red cells were placed into sodium chloride for approximately 2-3 minutes, the solutions were centrifuged to pellet any unlysed cells. Supernatant solutions then were subjected to spectrophotometric analysis to determine the hemoglobin concentrations. Percent lysis is determined by comparing hemoglobin concentrations of each sample to a totally lysed control. Free hemoglobin concentration was relatively low until approximately 0.5 grams sodium chloride per 100 ml was reached and then hemoglobin is released immediately. By comparison with the red cell fragility results, the volume changes were directly correlated to hemoglobin release. Furthermore, hemoglobin release was the same in labelled and unlabelled cells.

To test in vivo stability of cells cyanine dye labelled according to the presently invented method, rabbit red cells were withdrawn, labelled with $DiSC_{14}(5)$, and reinfused. Periodically thereafter, blood samples were obtained and analyzed for percent labelled cells and fluorescence intensity of the labelled cells. The number of circulating red cells decreased linearly as a function of time and the measured 52 day lifetime of labelled cells correlated closely with the 40 to 60 day average reported life time of rabbit red cells. Thus, cyanine dye labelling did not affect the clearance rate of red blood cells.

In all but one of the five rabbits tested, fluorescence intensity of the stained cells remained essentially unchanged 60 days after labelling and reinjection. In the fifth animal, not more than 20% of the cyanine dye had migrated from the labelled cells after 60 days in the rabbits' circulation. These data combined with data from tissue culture showing no transfer of dye from labelled to unlabelled cells demonstrate that the cells are stably labelled with the dYes.

Viable cells labelled with cyanine dyes according to the present invention are used in numerous applications requiring the ability to distinguish multiple subpopulations of a population of cells. For example, to determine whether post red blood cell transfusion reductions in hematocrit result from bleeding or immunologic reaction to the transfused cells, prior to transfusion an aliquot of the cells is labelled according to the present invention and immediately after transfusion a determination of the fraction of labelled red cells in circulation is made. Thereafter, upon finding a falling hematocrit the fraction of labelled cells is compared to that immediately after transfusion and an evaluation of the relative rates of reduction for labelled and unlabelled cells is made. Equivalent reductions in labelled and unlabelled cells indicates blood loss caused by bleeding, whereas greater reductions of the labelled cells indicates an immunologic reaction to the transfused cells. Using similar methodology, post platelet transfusion reductions in platelet count caused by bleeding can be distinguished from immunologic reactions to the transfused platelets.

The presently invented method also is used to determine growth rate of cultured mammaliah cells. Each time labelled cultured cells divide, the cyanine dye is evenly distributed between the daughter cells. Therefore, using flow cytometric techniques to compare fluorescence intensity of the cells after some period of growth to fluorescence intensity immediately after labelling, the number of cell divisions and thus the growh rate can be determined.

The following examples illustrate the present invention and are not intended to limit the scope of the invention as defined above and claimed below.

EXAMPLE 1

Method for Staining Tissue Culture Cells

I. Preparation of Cells

Log phase tissue culture cells are used to obtain best results. Suspension cultures are removed from the culture vessel and placed into polypropylene centrifuge tubes.

When using monolayer cultures, supernatants must be removed and the adherent cells washed with calcium and magnesium free phosphate buffered saline solution to remove serum proteins from the flask. Trypsin-EDTA solution (Gibco Laboratories, Grand Island, N.Y., #610-5300) is added to cover the bottom of the flask and is allowed to incubate at room temperature until the cell monolayer is dislodged and disaggregated. The resultant cell suspension is transferred to a poylpropylene centrifuge tube and an equal volume of culture media containing 10% Fetal Bovine Serum (FBS) (Hazelton) is added to arrest the enzymatic action of the trypsin. Cells are centrifuged at 400 xg for ten minutes at room temperature. Supernatants are aspirated and an equal volume of iso-osmotic mannitol is replaced for resuspension of the cell pellet. This mannitol wash is to remove the plasma proteins from the cell suspension and prepare cells for staining. Cells are once again centrifuge at 400 xg for ten minutes at room temperature. The supernatants are aspirated and the resultant cell pellet is resuspended in mannitol solution at a concentration of $2 \times 10^6$ cells/ml for staining. Some cell lines, however, are sensitive to the use of a sugar alcohol (mannitol); in such cases an iso-osmotic glucose solution (MW 180.16, 54.05 g/l may be used.

Preparation of Stock Dye Solutions $2 \times 10^{-3}$M stock solutions are prepared as follows in absolute ethanol.

| | |
|---|---|
| DiO—$C_{14}$(3) | MW 800 (1.600 mg/ml) |
| DiS—$C_{14}$(5) | MW 814 (1.628 mg/ml) |
| DiO—$C_{18}$(3) | MW 936 (1.872 mg/ml) |
| DiI—$C_{14}$(5) | MW 850 (1.700 mg/ml) |

All dyes are obtained from Molecular Probes, Eugene, Oreg.

Dye stocks are sonicated to insure complete solubility of the dye and to minimize adherence to the tubes. Polystyrene tubes are used for preparation of stock solutions so that solubility of the dye can be observed. Polypropylene tubes, however, are used to stain cells because cyanine dyes in an aqueous environment are much less adherent to polypropylene when compared to polystyrene.

III. Cell Staining

Cells are adjusted to a concentration of $2 \times 10^6$ cells/ml in iso-osmotic mannitol. To stain cells, $2 \times 10^{-3}$M stock dye solution is added to the staining solutions at 5 $\mu$l of dye per 1 ml of cell suspension. The sample for staining is pipetted or vortexed to thoroughly mix the sample. Cells are incubated with the dye for ten minutes, after which a small aliquot is removed for examination under a fluorescent microscope to insure that intense and uniform staining has occurred. The DiO dye series uses microscope filters selective for 488 nm excitation light, while the DiS and DiI dye series requires excitation near 575 nm for observation of fluorescence.

After the incubation period, an equal volume of phosphate buffered saline (PBS) is added to the stain-cell suspension. The cells are centrifuged at 400 xg for ten minutes at 20° C. The supernatant is aspirated and the pellet is resuspended in PBS. The centrifugation procedure is repeated and the resultant supernatant is observed for the presence of dye. If dye is apparent in the supernatant, washing is repeated until the supernatants are devoid of free dye as measured by spectrofluorometry. After the final wash, the supernatant is removed and the pellet resuspended to the desired concentration in a suitable culture medium. All procedures are performed under sterile conditions.

EXAMPLE 2

Red Blood Cell Staining

I. Reagent Preparation

A. Citrate Anticoagulant

| | |
|---|---|
| 1.66 g | NaCitrate |
| 0.206 g | Citric Acid |
| 0.140 g | NaH$_2$PO$_4$ |
| 1.61 g | Glucose |

The listed components are dissolved in 63 ml of distilled water and the solution is adjusted to a pH of 5.6. The final solution is passed through a 0.22 micron filter for sterilization.

B. Iso-osmotic Glucose Solution

Glucose (54.05 g) is dissolved in one liter of distilled water. The osmolarity is checked using a Fiske osmometer and adjusted to 320 mOsm if necessary.

II. Preparation of Stock Dye

A stock solution of $2 \times 10^{-3}$M DiIC$_{14}$(5) is prepared by dissolving 1.628 mg/ml of dye in absolute ethanol. Sonication may be required to completely solubilize the dye.

III Staining Procedure

Whole blood is collected aseptically using vacutainers containing sodium citrate or a syringe containing prepared citrate anticoagulant in an amount equal to one tenth the total volume of the syringe. A small aliquot is reserved for flow cytometry or functionality testing. The blood is centrifuged at 100 xg for ten minutes at room temperature to pellet red cells. The plasma containing platelets is removed and reserved, and the red cells are washed by adding iso-osmotic glucose in an amount equal to five times the volume of the packed red cell pellet. The cells should again be centrifuged at 100 xg for ten minutes at room temperature and the supernatant aspirated. This wash which removes the plasma proteins and allows for more intense and uniform staining is repeated one more time. After the final centrifugation and aspiration of the supernatant, the red cells are resuspended in iso-osmotic glucose to a concentration of $4 \times 10^8$ cells/ml.

Prior to the addition of dye, the sample is pipetted or vortexed to insure that sedimentation has not occurred. Fifteen microliters of stock DiSC$_{14}$(5) (2 mM in ETOH) is added to each one milliliter of the red cell suspension. The sample is immediately mixed to insure rapid and uniform distribution of the dye in solution. After approximately five minutes a small aliquot is removed for microscopic observation. A ring is drawn on a glass microscope slide using a wax pencil and a small sample of the cells in staining solution is placed within the wax ring. A coverslip is placed on the slide and the sample is observed. The use of the wax ring lessens discocyte-echinocyte transformation due to the glass slide and coverslip. Use of plastic slides and coverslips will also prevent this transformation. In this way one can insure that the red cell structure is maintained throughout the staining procedure while insuring that intense and uniform staining has occurred. Cells should be uniformly stained after five minutes and exposure times of longer than ten minutes should not be necessary.

After it has been determined that the cells are uniformly stained, an equal volume of phosphate buffered saline is added to the staining suspension. Cells are centrifuged at 400 xg for ten minutes at room temperature, and the supernatant is removed. There will usually be traces of free dye visibly present in the supernatants after centrifugation and therefore the washing procedure using phosphate buffered saline containing calcium and magnesium must be repeated until the supernatants are devoid of free dye as measured by spectrofluorometry.

At this point cells may be either suspended in an appropriate solution for experimentation or platelet poor plasma for reinjection into a recipient animal. For reinjection the general method is to resuspend the stained red cells in the volume of plasma which was recovered from the first centrifugation of the collected whole blood and which has been centrifuged at 4000 xg to remove platelets. All procedures are performed using sterile techniques.

EXAMPLE 3

Staining of Platelets

I. Preparation of Cells

Whole blood is collected in vaccutainers containing sodium citrate or in syringes containing prepared sodium citrate anticoagulant in an amount equal to one tenth the total volume of the syringe. The cells are centrifuged at 100 xg for ten minutes at room temperature to obtain platelet rich plasma. Plastic pipets and polypropylene centrifuge tubes are used for all procedures involving platelets to prevent activation.

The platelet rich plasma is aspirated and transfered to another centrifuge tube. The platelets are then pelleted through the plasma by centrifuging at 1000 xg for ten minutes at 20° C. The plasma is then collected and reserved for either functionality testing or use as a suspension medium for reinjection. This plasma should be spun 4000 xg for ten minutes to insure that any residual platelets are removed before use as a resuspension medium, and is referred to as platelet poor plasma (PPP).

The platelet pellet obtained from centrifugation at 1000 xg, should be resuspended gently in a small volume of citate anticoagulant to obtain a concentrated uniform suspension. After this is achieved iso-osmotic glucose may then be added as a diluent, in an amount equal to the plasma originally present. The platelets are then centrifuged at 300 xg for five minutes and the supernatants are aspirated. This glucose wash removes residual plasma proteins and allows for uniform and more intense staining. The platelet pellet is resuspended in the glucose solution and is now ready for staining.

Platelet concentration is adjusted $4 \times 10^8$ cells/ml and 15 $\mu$l of stock $DiOC_{14}(3)$ (2 mM in absolute ETOH) is added per ml of platelet suspension. The suspehsion is immediately but gently and thoroughly mixed to insure even distribution of the dye. Platelets are observed using a fluorescent microscope to insure that uniform staining has occurred and if so are now ready for separation from the free dye in suspension.

II. Use of Sephadex G-100 Column for Separarion of Labelled Platelets

Sepharose 2B has been traditionally used to isolate platelets from platelet rich plasma. We have found that Sephadex G-100 also works well in the isolation of platelets. This technique is applied with the staining technology and works in the following manner. A platelet-dye suspension is loaded onto the column. The small molecular weight dye molecules become trapped within the particles while the large platelets are passed directly through the column. In this manner, Sephadex G-100 can be used to separate fluorescently labelled platelets from free dye in suspension.

A. Preparation of Column

Sephadex G-100 (Pharmacia Laboratories, Piscataway, N.J.) is hydrated according to the manufacturer's directions, and washed in acetone (100%) in preparation for use as a separation medium for platelets. The washing procedure is carried out by centrifuging the Sephadex at 300xg for ten minutes at room temperature, removing the supernatant and resuspending in Hanks Balanced Salt Solution. The Sephadex should be repeatedly washed with Hanks Balanced Salt Solution until the odor of acetone is no longer detected. The resultant solution is degassed by insertion in a boiling water bath by vacuum.

The Sephadex slurry is then used to pour a column. A 10 cc syringe without plunger is used as the column support. Silicone tubing is attached to the hub of the syringe and a small adjustable tubing clamp is used to regulate fluid flow through the column. Forty seven micron nylon mesh is used as a support at the base of the syringe to retain the Sephadex beads. Conventional glass columns with fritted glass filter supports should be avoided since these may serve to activate platelets. The column is filled with Hanks and small amounts of the Sephadex slurry are added to the column. The clamp is opened enough to allow for a slow but consistent flow. This procedure packs the Sephadex evenly and uniformly and prevents channels or air spaces from forming. The procedure of adding HBSS and Sephadex slurry is repeated until the desired size packed column is obtained. The column should be completely flushed with HBSS (2 void volumes) prior to use.

B. Separation of Platelets

The platelet dye and suspension is layered carefully over the Sephadex. The clamp at the bottom of the column should be opened and the fluid level in the column should be allowed to drop until it reaches the top of the Sephadex fluid. Resume flow to allow the suspension to penetrate the Sephadex. Curtail flow again when level is at the top of Sephadex. Add enough HBSS carefully to the top of the column to create a buffer so that additional HBSS can be added easily without disturbing the Sephadex. Again, resume flow of the column. Using this method allows the platelet suspension to form a tight band in the gel and migrate at a fairly uniform rate throughout the length of the column. In this way a more concentrated platelet eluant is obtained. Continue flow through the column, collecting 0.5 to 1.0 ml fractions. The platelet containing fractions will be visible by their opacity and may be pooled together. The pooled fractions are then centrifuged at 300 xg for ten minutes. The supernatant is aspirated and the pellet may be resuspended in a suitable media for experimentation or analysis, or platelet poor plasma for functionality determinations or reinjection.

The preferred embodiments of the invention are illustrated by the above, however, the invention is not limited to the instructions disclosed herein, and the right to all modifications within the scope of the following claims is reserved.

What is claimed is:

1. A method for labelling viable cells with a cyanine dye that comprises contacting the cell with a cyanine dye of the structure:

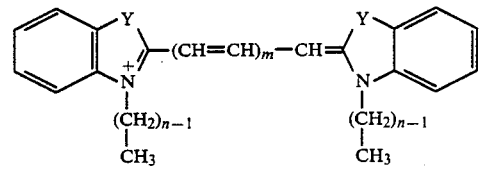

in which:
Y is oxygen, sulfur, methylene, or alkylsubstituted methylene;
m is 0-3; and
n is 12-22 in medium containing an osmolarity regulating agent that does not significantly affect cell viability and that provides for reproducible cell labelling, said agent being selected from the group consisting of a sugar, a sugar-alcohol, an amino acid, a Good's buffer and a combination thereof.

2. The method of claim 2 wherein the medium is iso-osmotic.

3. The method of claim 2 wherein the cell is a red blood cell.

4. The method of claim 2 wherein the cell is white blood cell.

5. The method of claim 2 wherein the cell is a platelet.

6. The method of claim 2 wherein the osmolarity regulating agent is a sugar.

7. The method of claim 6 wherein the sugar is glucose.

8. The method of claim 2 wherein the osmolarity regulating agent is a sugar-alcohol.

9. The method of claim 8 wherein the sugar-alcohol is mannitol.

10. The method of claim 2 wherein the osmolarity regulating agent is an amino acid.

11. The method of claim 10 wherein the amino acid is glycine.

12. The metnod of claim 2 wherein the osmolarity regulating agent is a Good's buffer.

13. The method of claim 12 wherein the Good's buffer is HEPPSO.

14. The method of claim 12 wherein the Good's buffer is EPPS.

15. The method of claim 12 wherein the Good's buffer is TAPS.

16. The method of claim 12 wherein the Good's buffer is CAPS.

17. The method of claim 12 wherein the Good's buffer is DIPSO.

18. The method of claim 2 wherein the cyanine dye is DiSC14(5).

19. The method of claim 2 wherein the cyanine dye is DiOC14(3).

20. A composition of matter comprising a cyanine dye of the structure:

[structure with substituents Y, N, $(CH_2)_{n-1}$, $CH_3$, and $-(CH=CH)_m-CH=$ linker]

in which
Y is oxygen, sulfur, methylene, or alkylsubstituted methylene;
m is 0—3; and
n is 12–22 dissolved in an osmolarity regulating agent that does not significantly affect cell viability, said agent being selected from the group consisting of a sugar, a sugar-alcohol, an amino acid, a Good's buffer and a combination thereof.

21. A composition of matter of claim 20 wherein the sugar is glucose.

22. A composition of matter of claim 21 wherein the sugar-alcohol is mannitol.

23. A composition of matter of claim 21 wherein the amino acid is glycine.

24. A composition of matter of claim 20 wherein the Good's buffer is HEPPSO, EPPS, TAPS, CAPS, or DIPSO.

25. A composition of matter of claim 20 wherein the cyanine dye is $DISC_{14}(5)$ or $DIOC_{14}(3)$.

26. The method of claim 2 wherein the cell is a tissue culture cell.

* * * * *